(12) United States Patent
Rane

(10) Patent No.: US 8,550,980 B2
(45) Date of Patent: Oct. 8, 2013

(54) KIT FOR LEVATOR AVULSION REPAIR

(75) Inventor: Ajay Rane, Townsville (AU)

(73) Assignee: AMS Research Corporation, Minnetonka, MN (US)

( * ) Notice: Subject to any disclaimer, the term of this patent is extended or adjusted under 35 U.S.C. 154(b) by 775 days.

(21) Appl. No.: 12/594,408

(22) PCT Filed: Apr. 4, 2008

(86) PCT No.: PCT/US2008/004394
§ 371 (c)(1),
(2), (4) Date: Jun. 25, 2010

(87) PCT Pub. No.: WO2008/124056
PCT Pub. Date: Oct. 16, 2008

(65) Prior Publication Data
US 2010/0263674 A1   Oct. 21, 2010

Related U.S. Application Data

(60) Provisional application No. 60/909,984, filed on Apr. 4, 2007, provisional application No. 60/979,288, filed on Oct. 11, 2007, provisional application No. 61/022,688, filed on Jan. 22, 2008.

(51) Int. Cl.
*A61F 2/00* (2006.01)

(52) U.S. Cl.
USPC .............................. 600/37; 600/29; 128/834

(58) Field of Classification Search
USPC ................................................ 600/29–32, 37
See application file for complete search history.

(56) References Cited

U.S. PATENT DOCUMENTS

| | | | |
|---|---|---|---|
| 4,741,330 A | 5/1988 | Hayhurst | |
| 5,368,602 A | 11/1994 | De La Torre | |
| 5,647,836 A | 7/1997 | Blake, III et al. | |
| 6,669,735 B1 | 12/2003 | Pelissier | |
| 2003/0212305 A1 | 11/2003 | Anderson et al. | |
| 2005/0245787 A1* | 11/2005 | Cox et al. ...................... 600/37 |
| 2005/0250977 A1* | 11/2005 | Montpetit et al. ............. 600/29 |
| 2006/0195011 A1 | 8/2006 | Arnal et al. | |
| 2006/0224038 A1 | 10/2006 | Rao | |
| 2007/0062541 A1 | 3/2007 | Zhou et al. | |
| 2008/0021265 A1 | 1/2008 | Garbin et al. | |
| 2008/0027271 A1 | 1/2008 | Maccarone | |
| 2008/0045782 A1 | 2/2008 | Jimenez | |
| 2010/0105979 A1 | 4/2010 | Hamel et al. | |
| 2010/0261952 A1 | 10/2010 | Monetpetit et al. | |

FOREIGN PATENT DOCUMENTS

| | | | |
|---|---|---|---|
| WO | WO03077772 A1 | | 9/2003 |
| WO | WO03096929 A1 | | 11/2003 |
| WO | WO2004045457 A1 | | 6/2004 |
| WO | WO2005110274 A1 | | 11/2005 |
| WO | WO 2006/069078 | * | 6/2006 |
| WO | WO2006069078 A2 | | 6/2006 |

(Continued)

*Primary Examiner* — Charles A Marmor, II
*Assistant Examiner* — Laura Fajardo
(74) *Attorney, Agent, or Firm* — Kagan Binder, PLLC

(57) ABSTRACT

Kits for treating pelvic conditions such as levator avulsion, by placing an implant between an anterior incision and a posterior incision to support the levator tissue are described. A kit comprises an implant (70) comprising a support portion and two end portions extending from the support portion, two insertion tools comprising a needle comprising a helical curve and one insertion tool (54) comprising a needle (58) comprising a two-dimensional curve.

13 Claims, 11 Drawing Sheets

(56) References Cited

FOREIGN PATENT DOCUMENTS

| | | |
|---|---|---|
| WO | WO2007059368 A1 | 5/2007 |
| WO | WO2007081955 A1 | 7/2007 |
| WO | WO2007146784 A2 | 12/2007 |
| WO | WO2007149348 A2 | 12/2007 |
| WO | WO2008013867 A1 | 1/2008 |
| WO | WO2008015722 A1 | 2/2008 |
| WO | WO2008042438 A2 | 4/2008 |
| WO | WO2008057269 A1 | 5/2008 |
| WO | WO2008083394 A2 | 7/2008 |
| WO | WO2008124056 A1 | 10/2008 |
| WO | WO2009005714 A2 | 1/2009 |
| WO | WO2009011852 A1 | 1/2009 |
| WO | WO2009038781 A1 | 3/2009 |
| WO | WO2009075800 A1 | 6/2009 |
| WO | WO2009145911 A1 | 12/2009 |
| WO | WO2010129331 A2 | 11/2010 |

* cited by examiner

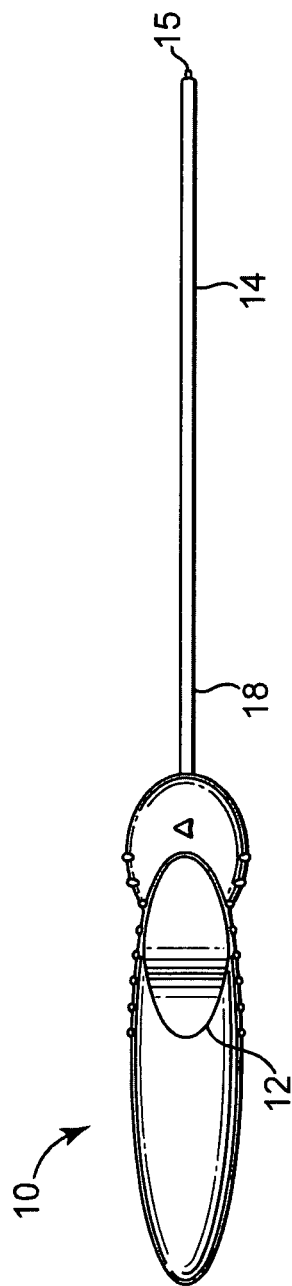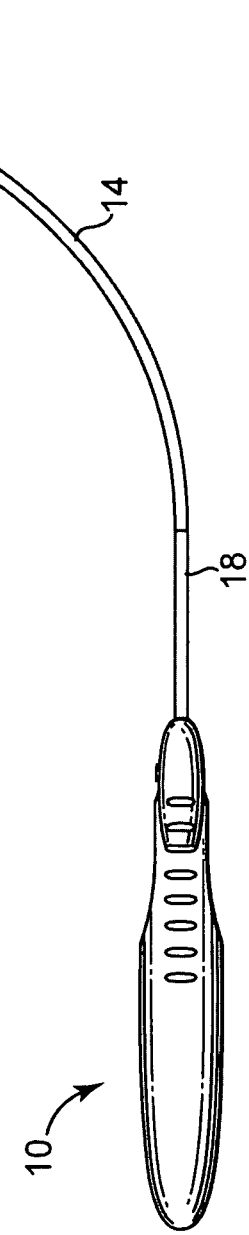
Fig. 4A
Fig. 4B

KIT FOR LEVATOR AVULSION REPAIR

PRIORITY CLAIM

The present patent Application claims benefit from International Application No. PCTUS2008/004394, which was filed on 4 Apr. 2008, which in turn claims priority to U.S. Provisional Patent Application having Ser. No. 61/022,688, filed Jan. 22, 2008, by Ajay Rane, titled TRA SYSTEM AND METHOD FOR LEVATOR AVULSION REPAIR; U.S. Provisional Patent Application having Ser. No. 60/979,288, filed on Oct. 11, 2007, by Ajay Rane, and titled SYSTEM AND METHOD FOR LEVATOR AVULSION REPAIR; and U.S. Provisional Patent Application having Ser. No. 60/909,984, filed on Apr. 4, 2007, by Ajay Rane, and titled SYSTEM AND METHOD FOR LEVATOR AVULSION REPAIR, wherein the entireties of said patent applications are incorporated herein by reference.

FIELD OF THE INVENTION

The invention relates to apparatus and methods for conditions of the pelvic floor by use of a pelvic implant to support pelvic tissue. The pelvic conditions include conditions of the levator muscle such as a levator avulsion, such as in a female patient, and related conditions such as incontinence, prolapse, and levator ballooning, among others.

BACKGROUND

Pelvic health for men and women is a medical area of increasing importance, at least in part due to an aging population. Examples of common pelvic ailments include incontinence (fecal and urinary) and pelvic tissue prolapse (e.g., female vaginal prolapse). Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

One specific area of pelvic health is trauma of the pelvic floor, e.g., of the levator ("levator ani") or coccygeus muscle (collectively the pelvic floor). The pelvic floor is made up of the levator and coccygeus muscles, and the levator is made up of components that include the puborectalis muscle, the pubococcygeus muscle, and the iliococcygeous muscle. For various reasons, the levator may suffer weakness or injury that could potentially result in various secondary conditions such as prolapse, incontinence, levator ballooning, and other conditions of the pelvis.

SUMMARY

Levator avulsion is the condition of trauma at levator tissue, such as perforation or tearing of a portion of the levator muscle, or detachment of the muscle from connective tissue or bone. Levator avulsion can often occur at the level of attachment of the levator to the obturator internus and ischial spine. The present application describes methods for treating a condition of levator avulsion in a manner that approximates levator tissue to remedy the avulsion, possibly replacing the position of the levator muscle in the region of the avulsion or reattaching the levator avulsion to the obturator internus muscle, the area around the ischial spine, or both. The present system may prevent genital prolapse and levator ballooning, as well as subsequent prolapse, incontinence, and similar conditions. During the procedure, isolated rectoceles or enteroceles may also be treated to prevent levator ballooning. The approach may also be used to treat fecal incontinence. The inventor's research suggests levator avulsion could be the missing link between childbirth and genital prolapse.

Exemplary methods, tools, and implants as described involve an elongate implant that is implanted in a position of a pelvic region in a manner to place a support portion of the implant at a region of a levator avulsion to support the levator tissue and remedy the avulsion. End or extension portions of the implant can extend to contact pelvic tissue in a manner that will cause the implant to support the levator tissue to treat the avulsion. The elongate implant can be placed to treat the avulsion through any one or more of the vaginal incision, anterior incision (e.g., at a position adjacent to a patient's obturator foramen), or posterior incision. When placed, the support portion of the implant will support the avulsed tissue and one end portion of the implant will extend through a tissue path leading to the anterior incision and one end portion of the implant will extend through a tissue path leading to the posterior incision.

In one aspect the invention relates to a method of treating a levator avulsion. The method includes: making a vaginal incision; making a posterior incision; making an anterior incision that allows access to an obturator foramen; palpating levator muscle through the vaginal incision to identify a levator avulsion; making a posterior tissue path between the posterior incision and a region of levator muscle in a region of the levator avulsion; making an anterior tissue path between the anterior incision and the region of levator muscle, through the obturator foramen; providing an elongate implant comprising a support portion and two end portions; passing an end portion through the anterior tissue path; passing an end portion through the posterior tissue path; positioning the support portion to contact tissue of the levator muscle at a location in the region of the levator avulsion; and tensioning the implant to approximate tissue of the levator muscle, to support the levator muscle, and to relieve the levator avulsion.

In another aspect the invention relates to a method of treating a levator avulsion. The method includes: making a vaginal incision at a posterior of a vagina; dissecting tissue of a pararectal space; palpating tissue through the vaginal incision to identify a levator avulsion; making a posterior incision lateral and posterior to the anus in a skin of a buttock; making an anterior incision at a location where an inferior edge of pubic ramus bone ends at a bottom of an obturator foramen; making a posterior tissue path between the posterior incision and a region of levator muscle in a region of the levator avulsion; making an anterior tissue path between the anterior incision and the region of levator muscle, through the obturator foramen; providing an elongate implant comprising a support portion and two end portions; passing a portion of one end portion through the anterior tissue path; passing a portion of the other end portion through the posterior tissue path; positioning the support portion to contact tissue of levator muscle; and tensioning the implant to approximate tissue of the levator muscle to support the levator muscle and relieve the levator avulsion.

In another aspect the invention relates to a kit for treating a levator avulsion, the kit including: an implant comprising a support portion and two end portions extending from the support portion; two insertion tools comprising a needle comprising a helical curve, and one insertion tool comprising a needle comprising a two-dimensional curve.

The following patent documents include information related to pelvic implants, tools, and methods for treating pelvic condition, and are incorporated herein by reference: U.S. Pat. Nos. 6,652,450; 6,612,977; 6,702,827; 6,802,807; 6,641,525; 7,037,255; 6,911,003; 7,070,556; 2005/0245787; 2005/0250977; 2003/0130670; 2004/0039453; and 2004/0249473.

BRIEF DESCRIPTION OF THE DRAWINGS

FIGS. 4A and 4B illustrate exemplary tools according to the description.

Figure 1:
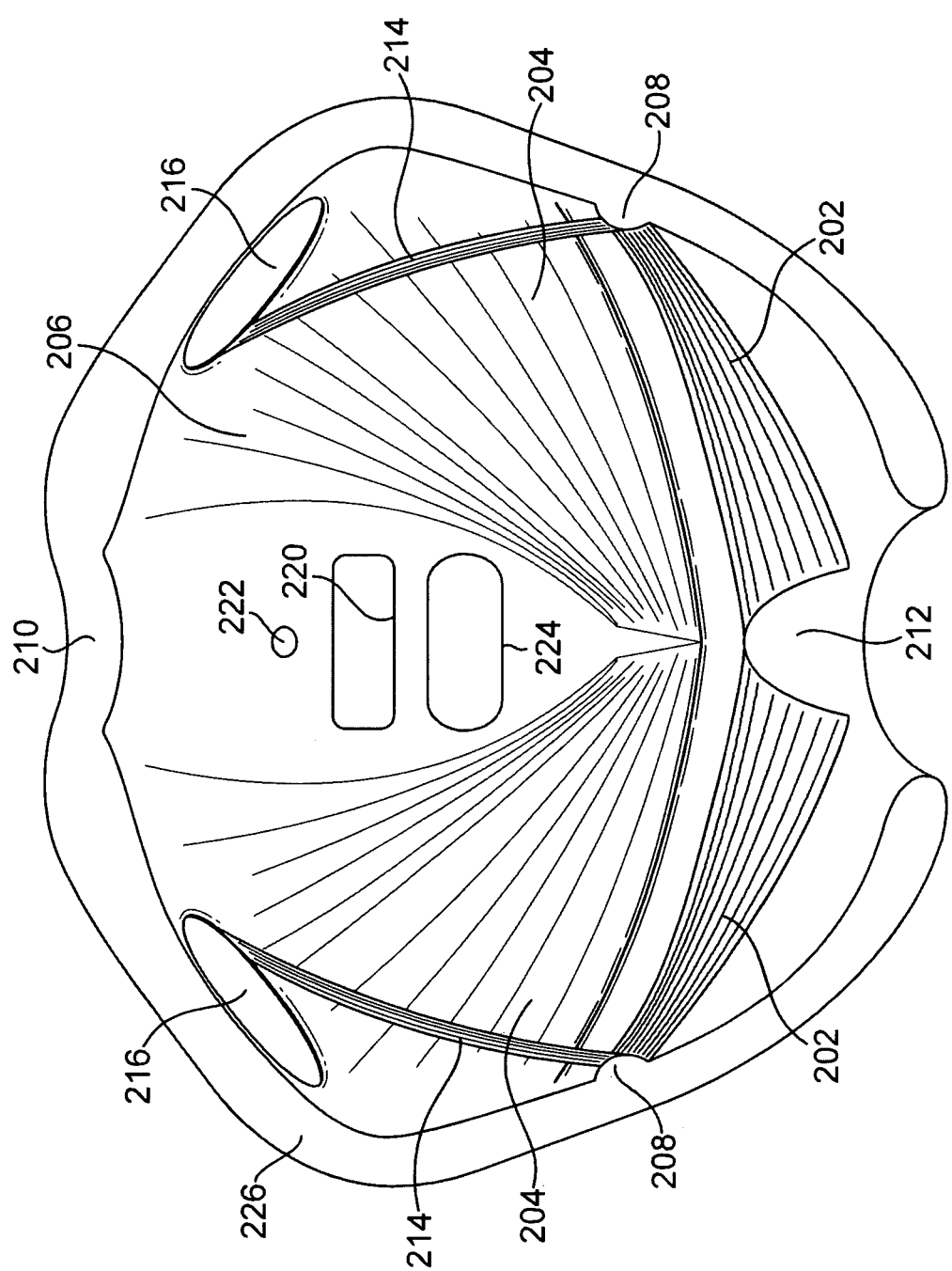
FIG. 1 shows general anatomy relevant to the present description.

All drawings are schematic and not to scale.

DESCRIPTION

The following description is meant to be illustrative only and not limiting. Other embodiments of this invention will be apparent to those of ordinary skill in the art in view of this description.

The invention relates to surgical implants, insertion tools, kits, and assemblies, and related methods for treating pelvic floor disorders related to levator avulsion. As a secondary effect the methods of treating levator avulsion may treat, improve, or prevent a condition such as prolapse, incontinence (urinary or fecal incontinence), conditions of the perineal body, conditions of the levator hiatus, levator ballooning, and combinations of two or more of these.

According to various embodiments, a surgical implant can be used to support levator tissue in a region of a levator avulsion. The implant is placed to contact levator tissue at a location in a region of a levator avulsion. A "region of a levator avulsion" refers to a location of levator tissue that can be contacted by a support portion of an implant to allow the implant to be manipulated or tensioned in a manner that will cause approximation of tissue of the levator muscle, to at least in part remedy the avulsion; the region may be at a surface of the levator tissue or at a location at an interior of the tissue, and may be at a location that is considered to be either "inferior" to ("caudal" to) the avulsed tissue or "superior" to the avulsed tissue; optionally the region can be proximal to the avulsion, such as within 3 centimeters, within 2 centimeters, or within 1 centimeter from tissue of an avulsion. As an example, a portion of implant (e.g., a portion of support portion, such as a short length of the support portion) can be placed within the tissue of the levator muscle ("embedded" in the muscle or "tunneled" through a length of the muscle). According to such an example, a portion of implant may enter (or exit) levator tissue on the vaginal side of the muscle inferior to the avulsed tissue, be embedded in the belly of the levator muscle and extend through (i.e., tunnel through) levator tissue in a superior (and optionally anterior) direction toward the avulsed tissue. The implant may optionally extend toward, to, or through, tissue of the avulsion, then exit (or enter) the levator muscle tissue on the side of the muscle facing the obturator foramen, either inferior to or superior to the avulsion. For instance the implant may tunnel from the described entry point on the vaginal side of the levator tissue to an exit point on an inferior side of the avulsion or at the avulsion, then extend toward the obturator foramen. Alternately, the implant may extend through the levator muscle tissue inferior to the avulsed tissue, traverse the avulsion, and continue to tunnel through levator tissue on a superior side of the avulsion, then exit (or enter) the levator tissue at a location superior to the avulsed tissue, such as at a location near the obturator internus muscle at the level of the ischial spine. Generally, the implant can exit the levator muscle tissue on the obturator internus side of the levator muscle, extend through tissue of the obturator internus muscle, through the obturator foramen, toward the anterior external incision, and exit the patient at the anterior incision.

The implant can be used to support the levator tissue to remedy a levator avulsion such as by approximating levator tissue, supporting levator tissue, or both, to cause levator tissue to move to close the avulsion. In the event that an avulsion involves a detachment of levator tissue from tissue or bone at a superior region of levator tissue—e.g., a detachment at or near tissue of an arcus tendineus, tissue of an obturator internus muscle, a pubic bone, an ischial spine, or any combination of these—the levator tissue can be approximated in a direction to allow the detached tissue to be moved closer to the location of the detachment. After this tissue approximation, the implant can be maintained in the implanted position to continue to support the levator tissue to prevent subsequent return of the levator muscle to the avulsed condition, and to potentially prevent future conditions of avulsion or related prolapse, incontinence, levator ballooning, or other pelvic condition.

FIG. 1 shows anatomy relevant to methods and devices of embodiments of the invention. Referring to FIG. 1, illustrated is a superior view of tissue at different levels of the pelvic region, including ischiococcygeous muscle 202, iliococcygeus muscle 204, puborectalis and pubococcygeous muscles 206, ischial spine 208, pubic symphasis 210, coccyx 212, arcus tendineus 214, and obturator foramen 216. Vagina 220, urethra 222, rectum 224, and pelvic bone 226 are also shown.

Referring to FIG. 1, a levator avulsion (not illustrated) may typically be located along the superior portion of the levator muscle extending between the ischial spine, along the arcus tendineus, and to the obturator internus muscle, for example at a superior portion of any one or more of the puborectalis muscle, pubococcygeus muscle, or iliococcygeous muscle. According to embodiments of the invention, an implant can be placed to approximate, support, or approximate and support, one or more of these muscles to treat the avulsion.

Figure 2:
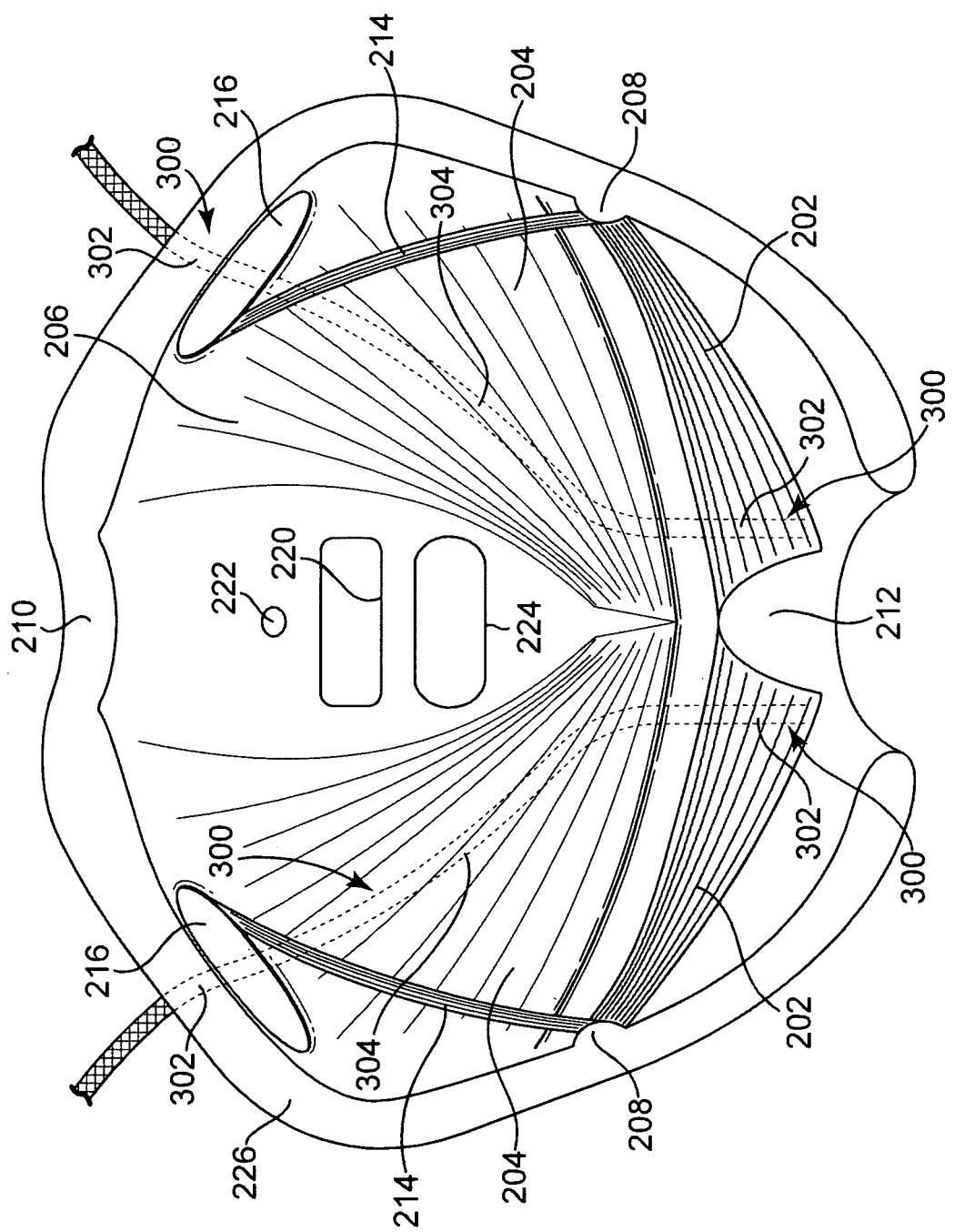
FIG. 2 shows anatomy and an example of an implant, implanted in a patient according to the description.

Referring to FIG. 2, this figure illustrates two opposing implants (e.g., mesh, tape, or the like) implanted according to certain general embodiments of the present description. (Dashed lines representing the location of implant 300 are indicative of the general tissue path between an anterior incision and a posterior incision, and the placement of the implant relative to muscle tissue of the pelvic floor is not limited by this diagram.) Left side mesh 300 and right side mesh 300 each include two end portions 302 extending in opposite directions from support portion 304. When installed to treat an avulsion, as shown, support portion 304 is placed at a region of the levator avulsion (the avulsion is not shown), so that the support portion can contact tissue of levator muscle and be tensioned to approximate tissue of the levator muscle in a direction and to a degree that will treat the avulsion. A portion of the implant, such as a portion of the support portion, may be located within the levator muscle tissue with a length of the implant tunneling through the levator muscle tissue (either superior to the avulsion or inferior to the avulsion, or both). Alternately, an implant may be located at a lower surface of the levator muscle such as below (i.e., on an inferior or caudal surface of) the levator muscle tissue, or may perforate or exit or enter the levator muscle tissue (e.g., superior to or inferior to the avulsed tissue). A portion of the implant may enter levator tissue at an inferior side of the avulsion on a vaginal side of the levator tissue, pass through levator tissue and optionally tunnel through the levator tissue toward the avulsed tissue, optionally pass through the avulsion, further pass through levator tissue on a superior side of the avulsion, exit the levator tissue just superior to a the avulsion (e.g., superior to a palpated avulsion site), and further pass through the obturator foramen and anterior incision.

As illustrated, one end portion 302 can extend from support portion 304 in an anterior direction through obturator foramen 216, and through an anterior incision (not shown) at the inner thigh of the patient. The other end portion 302 of the same implant extends from support portion 304 in a posterior direction to a posterior incision (not shown) in a perirectal region, optionally passing through posterior tissue of the pelvic region such as one or more of levator muscle, coccygeous muscle, gluteus muscle, skin, sacrotuberous ligament, ischorectal fossa, fat, iliococcygeus muscle, and puborectalis muscle.

Figure 6A:
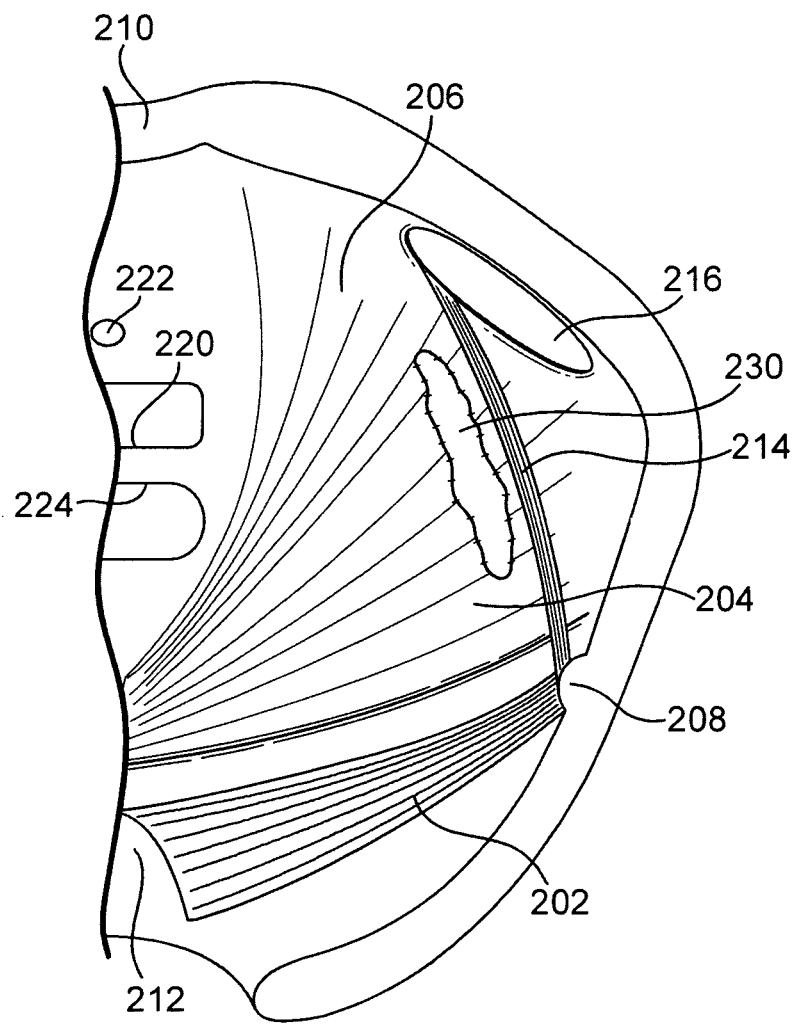
FIG. 6A illustrates relevant anatomy and depicts an exemplary levator avulsion.
Figure 6B:
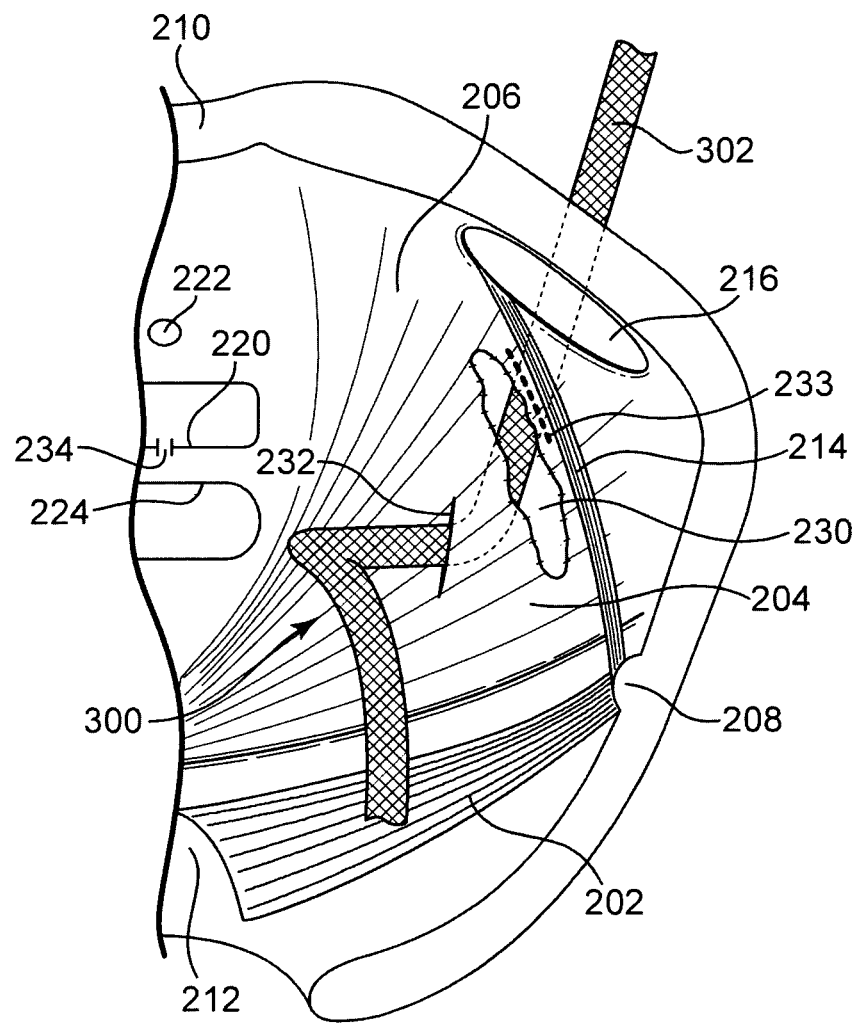
FIGS. 6B, 6C, and 6D illustrate an example of an implant, implanted in a patient according to various embodiments of the description.
Figure 6C:
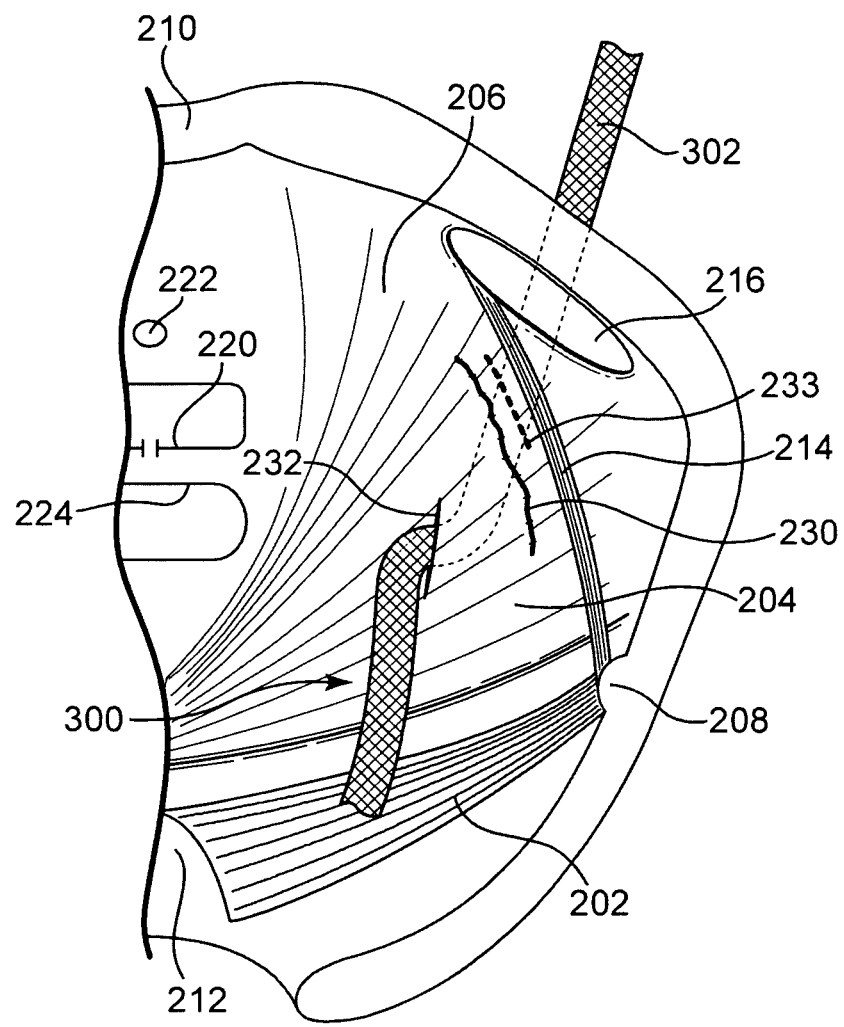

FIG. 6A illustrates relevant anatomy (on a patient's right side), as described, and includes an exemplary depiction of avulsion 230. FIG. 6B shows one exemplary embodiment of placement of implant 300. Implant 300 enters (or exits) levator tissue at entry point 232 (solid line), illustrated to be on a superior surface of levator muscle (the surface that is on the vaginal tissue side of the levator muscle) and inferior to avulsion 230. Implant 300 then extends from entrance point 232 through and within levator tissue by tunneling through the levator muscle tissue toward avulsion 230. In this embodiment, implant 300 passes through avulsion 230 and then enters tissue on the superior side of the avulsion, tunneling through the levator tissue on the superior side of the avulsion and exiting the levator tissue on the obturator foramen side of the levator tissue at exit point 233 (shown in dashed lines). From exit point 233 implant 300 extends through the obturator foramen (e.g., though the obturator internus muscle) and exits the patient through the anterior incision. As illustrated at FIG. 6B, implant 30 may be introduced to the illustrated anterior tissue path through a vaginal incision (234); alternately implant 30 may be introduced to the illustrated tissue path transcutaneously either through an anterior incision or a posterior incision. Upon tensioning the implant, e.g., by placing traction or tension at end portion 302 (preferably anterior end portion 302), avulsion 230 is at least partially repaired, as shown at FIG. 6C. FIG. 6C also shows implant 300 extending in a posterior direction through a posterior tissue path as described, and to and through a posterior incision (not shown).

Figure 6D:
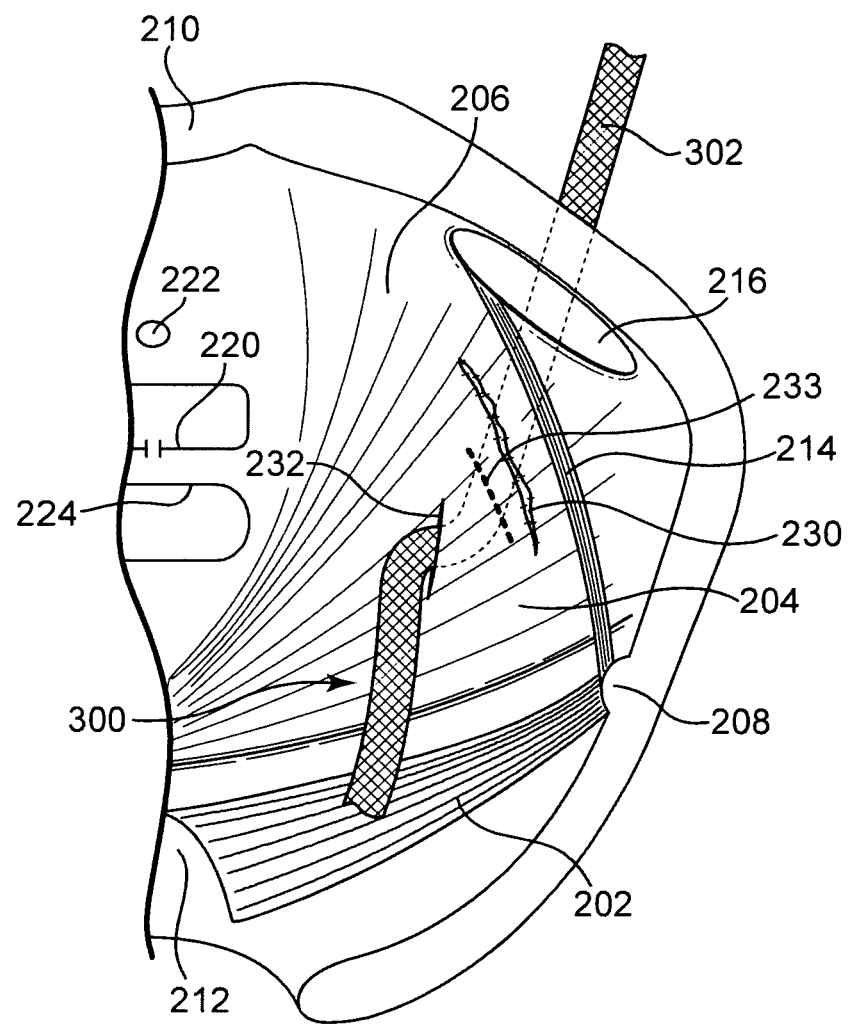

FIG. 6D shows another exemplary embodiment of placement of implant 300 through an anterior tissue path as described herein. Implant 300 enters (or could be considered to exit) levator tissue at entry point 232 on a superior surface of levator muscle (the surface that is on the vaginal tissue side of the levator muscle) and inferior to avulsion 230. Implant 300 then extends from entrance point 232 through and within levator tissue by tunneling through the levator muscle tissue toward avulsion 230. In this embodiment, implant 300 passes to a location near but still inferior to avulsion 230 and then exits the levator tissue in an anterior direction from exit point 233 (shown in dashed lines), which is inferior to avulsion 230. (In still another alternate embodiment implant 300 can exit the levator tissue at the avulsion.) From exit point 233 implant 300 extends through the obturator foramen (e.g., though the obturator internus muscle) and exits the patient through the anterior incision. The implant may be introduced transvaginally or transcutaneously through an anterior or a posterior incision. Upon tensioning the implant, e.g., by placing traction or tension at end portion 302 (preferably anterior end portion 302), avulsion 230 is at least partially repaired, optionally by causing tissue of the avulsed levator muscle to move toward obturator internus muscle or arcus tendineus tissue.

The implant can be placed and extend through an anterior incision, a posterior incision, and tissue paths that extend (on one or both sides of a patient) between the three locations of the anterior incision, the region of the levator avulsion, and the posterior incision.

An anterior incision can be at a region of the inner thigh or groin area adjacent to an obturator foramen. An anterior tissue path into or through which an implant or portion of an implant can be placed can be created between the anterior incision and a region of the levator avulsion. Such a tissue path can extend through an obturator foramen. Features of useful anterior external incisions and anterior tissue paths are described at United States Patent Application 2005/0250977 (Ser. No. 10/840,646), the entirety of that document being incorporated herein by reference.

A posterior incision can be in a perirectal region generally posterior to and lateral to the anus. A posterior tissue path into or through which an implant or portion of an implant can be placed can be created between the posterior incision and the region of the levator avulsion. Such a tissue path can extend through muscle tissue at a posterior location of the pelvic region such as gluteus muscle, levator muscle, coccygeous muscle, or nearby tissue. An example of an external posterior incision is of the type described at United States Patent Application 2007/0068538 (Ser. No. 11/518,932), the entirety of that document being incorporated herein by reference.

A vaginal incision can be used to access the interior portion of the pelvic region, such as for palpation, to allowing movement (guidance) of an insertion tool, or to connect an end of an implant with a tip of an insertion tool. A vaginal incision can be created at a position to allow access to the pelvic region, especially levator tissue, avulsed levator tissue, landmarks such as the ischial spine, and posterior tissue such as coccygeous muscle. Particular utility of a vaginal incision is the ability to palpate levator tissue, tissue of an ischial spine, and tissue of a levator avulsion, during a procedure. Additionally, a vaginal incision can allow access to the interior pelvic region to allow a surgeon to guide or place an implant or a needle (implantation tool). Associated with a vaginal incision, such as a posterior vaginal incision, can be a posterior dissection to provide access to tissue such as an ischial spine, levator muscle, coccygeous muscle such as pubococcygeous muscle, levator muscle, glueal muscle, etc. An exemplary vaginal incision can be made at a location along the posterior wall from the vault to the perineal body, affording access to the ischial spine, iliococcygeus muscle, and also a caudal or inferior portion of the obturator internus muscle.

One or more tissue paths can be made in any desired general direction starting or ending at either external incision, or starting or ending at the vaginal incision or at a region of levator muscle or the levator avulsion. Generally the tissue path can be made to allow a portion of the implant to be placed between an external incision (the anterior or the posterior incision) and the region of the levator avulsion. A method of implanting an implant as described does not require the use of any particular number of tissue paths, tools, any style of tool or implant, or any particular direction of dissection when preparing a tissue path or inserting an implant or a portion of an implant. For example, the implant or a portion of implant may be inserted through either external incision or through a vaginal incision. Also, the implant or a portion of implant can be guided through a tissue path using an insertion tool by either pushing the needle to pull the implant into the tissue path or by pulling the tool to pull the implant through the tissue path.

One example of a particular method of preparing anterior and posterior tissue paths can be a method performed with only a single insertion tool. Generally, a needle of the tool can be inserted at either one of an external anterior or an external posterior incision, passed to a region of the levator avulsion, and then further passed to the other external incision. A vaginal incision can be useful in this type of procedure for palpation and to allow a surgeon to guide the needle tip. The tissue path can pass through tissue as described herein, such as an anterior tissue path that extends between an anterior external incision, through an obturator foramen (e.g., through obturator internus muscle), to a region of levator avulsion, optionally contacting a surface of levator tissue, tunneling through levator tissue, or perforating levator tissue. A posterior tissue path can extend between the region of levator avulsion, optionally contacting a surface (inferior or superior surface) of levator tissue, tunneling through levator tissue, or perforating levator tissue, and at a location posterior to the levator avulsion optionally passing through posterior pelvic tissue such as dissected or perforated posterior muscle or other tissue (e.g., levator tissue, coccygeous muscle, pubococcygeous muscle, iliococcygeous muscle, fat, fossa), through gluteus muscle, and to the posterior external incision (through the skin).

When using a single needle to form a complete tissue path between the two external incisions, an end of an implant (e.g., comprising a connector secured to an end of an end portion) can be connected to a needle tip either before the needle is inserted into the patient and through the tissue path, or after the needle is positioned to extend through the patient between the two external incisions. The needle can be used either by pushing to lead the implant into place or to by pulling to pull the implant into place within the tissue path.

Figure 3A:
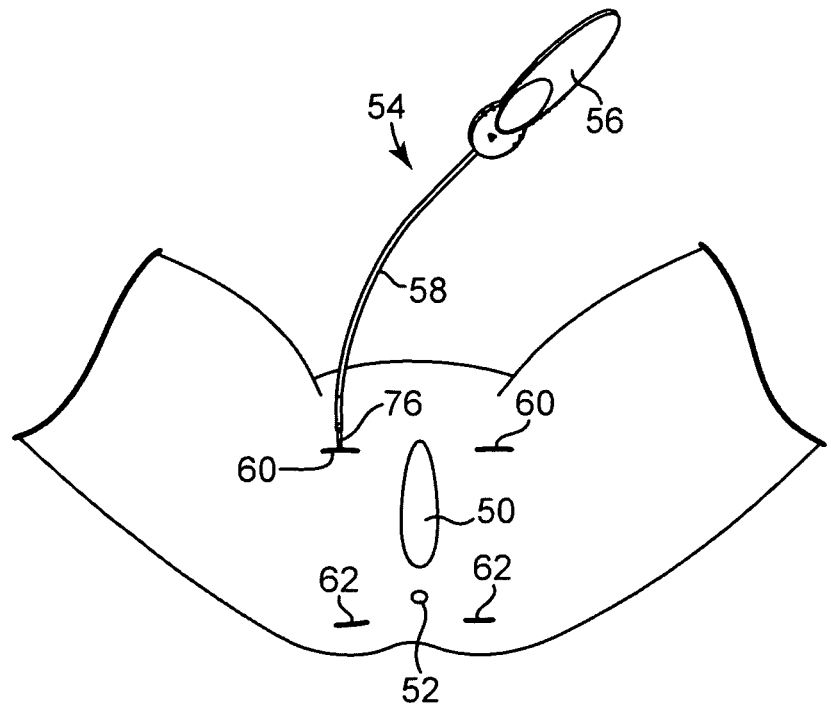
FIGS. 3A through 3D illustrate exemplary steps of an embodiment of a method as described.

An example of a method of using a single tool to create an anterior tissue path and a posterior tissue path is shown at FIGS. 3A through 3D. FIG. 3A shows an inferior view of a patient, with vagina 50, anus 52, and insertion tool 54 including handle 56 and needle 58, which is curved in two dimensions. Anterior incisions 60 and posterior incisions 62 are also shown.

Figure 3B:
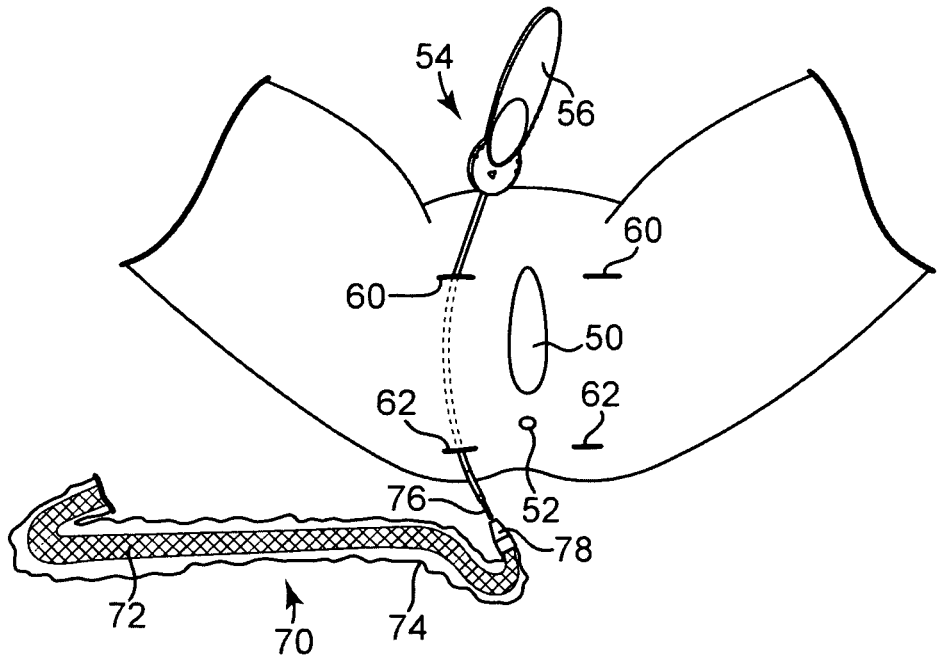
Figure 3C:
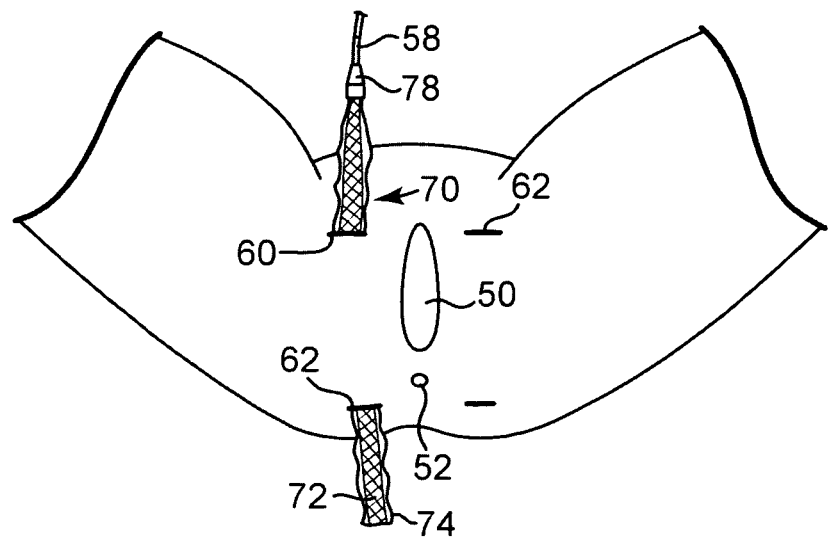

Referring to FIG. 3A, needle 58 has been inserted into anterior incision 60 on the patient's right side (typically a surgeon's left side). The needle is further inserted to create an anterior tissue path as described, which leads through the patient's right obturator foramen to a region of a levator avulsion; the needle then extends through a posterior tissue path between the region of levator avulsion to the posterior incision. As shown at FIG. 3B, when needle tip 76 has been extended from posterior incision 62, tip 76 can be connected to an end (e.g., connector 78) of implant assembly 70. Implant assembly 70 includes mesh strip 72 and connector 78, which is designed to engage tip 76 of needle 58. Plastic sheath 74 surrounds mesh strip 72. Optionally, mesh strip 72 can include an additional tensioning member (e.g., tensioning suture) (not shown) running along a portion of or the entire length of the mesh and connected to the mesh at multiple locations. After connecting connector 78 to tip 76, needle 58 can be withdrawn from the patient and implant assembly 70 is drawn through the tissue path from the posterior incision through the tissue path and through the anterior incision. See FIG. 3C. Needle 58 can be removed from implant assembly 78 such as by cutting the assembly mesh and sheath at a location near connector 78. The remaining portion of the implant assembly including sheath 74 and mesh strip 72 can be tensioned either before or after sheath 74 is removed by drawing the sheath away from mesh strip 72 and the patient. Tensioning can be performed by placing pressure on either end portion extending from either anterior incision 60 or posterior incision 62. Preferably, tensioning can be performed by placing traction on the portion of implant extending from anterior incision 60.

Figure 3D:
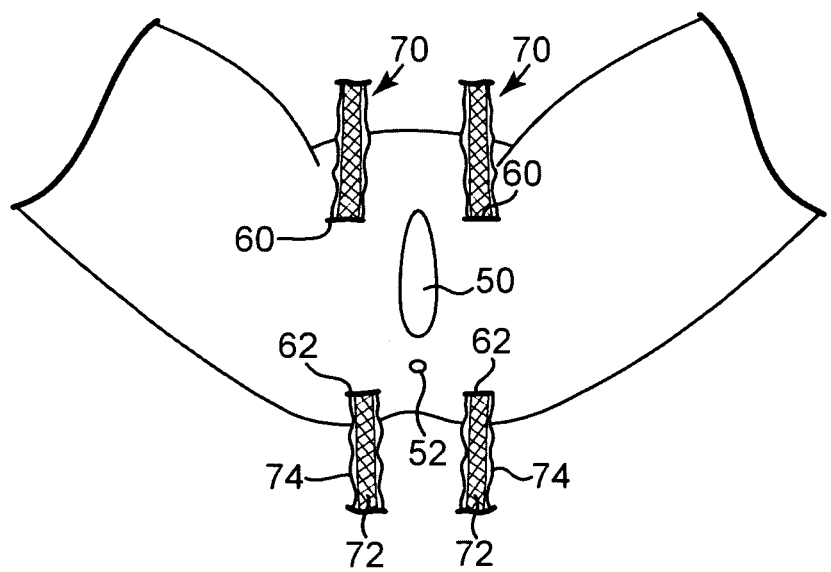
Figure 5A:
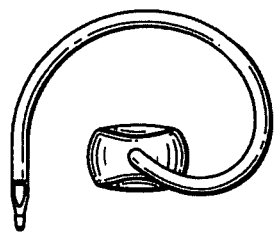
FIGS. 5A through 5D illustrate exemplary tools according to the description.
Figure 5B:
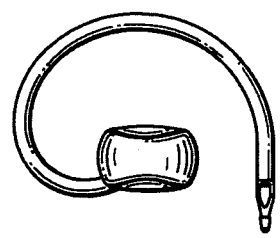
Figure 5C:
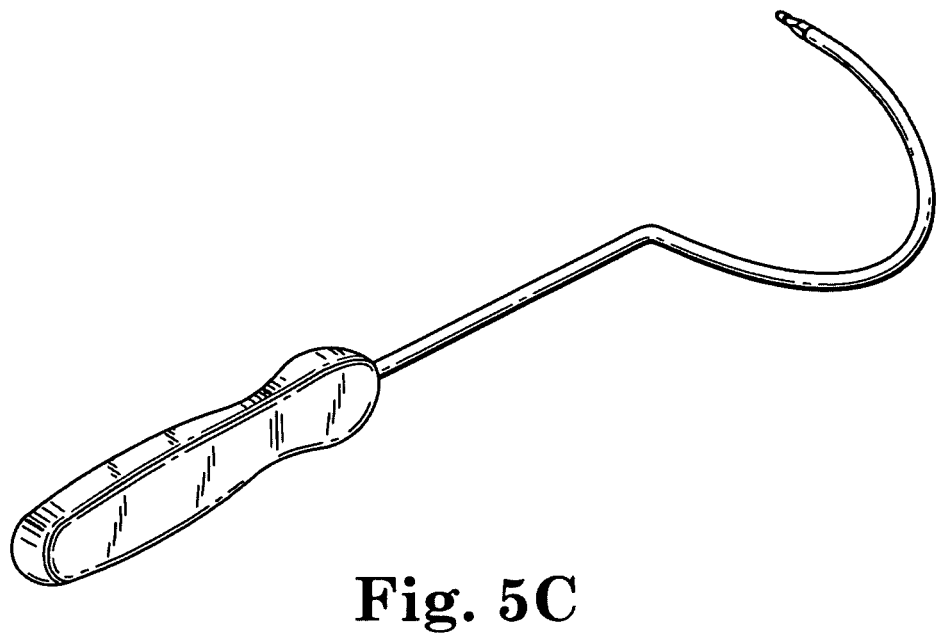
Figure 5D:
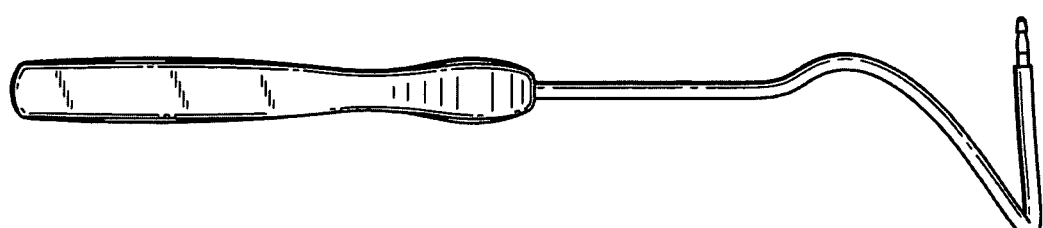

FIG. 3D shows a patient having two implant assemblies 70 installed, one on a patient's left side and one on a patient's right side. The method may involve placement of only one implant on one side of a patient, or two implants, one on each side of the patient. Alternate methods can place two or more implants on either a left side or a right side of a patient, both implants extending through a tissue path as described (although not necessarily identical tissue paths), and both implants extending through the same anterior incision and posterior incision.

The embodiment of the method illustrated at FIGS. 3A through 3D, which may be referred to as a "single needle embodiment," uses a single insertion tool extending between an anterior incision and a posterior incision (placed in this position in either direction between the anterior and posterior incisions). Such approach may be considered a transcutaneous approach, which passes a needle starting from one incision such as the anterior incision (at the groin), through the obturator foramen and then while palpating the needle in the belly of the puborectalis muscle (through the vaginal opening and optionally using a vaginal incision) causes the needle to tunnel through the levator muscle tissue in a region of the levator avulsion, further passes the needle to an exit at a location posterior and lateral to the anus. The tissue path can be made in either direction and the implant can be passed through this tissue path (a combined posterior tissue path and anterior tissue path) in either direction between the posterior and anterior incisions.

According to other embodiments of methods of implanting a sling to treat a levator avulsion, tissue paths can be prepared using alternate types of tools, such as two different tools, one tool to prepare an anterior tissue path and one tool to prepare a posterior tissue path. A tool for preparing a left-side tissue path can differ from a tool for preparing a right-side tissue path. Exemplary methods can use up to four tools for placing two implants, one on each of a patient's left side and a patient's right side. One tool can be used for each of a left-side anterior tissue path, a right-side anterior tissue path, a left-side posterior tissue path, and a right-side posterior tissue path.

As an example, multiple needles may be used to create different tissue paths or portions of different tissue paths, such as one needle to create an anterior tissue path from the anterior incision to a region of levator avulsion and another needle to create a posterior tissue path from the posterior incision to a region of levator avulsion. When two needles are used, an end of a needle may be connected to an end of an implant (e.g., connector) either before the needle is inserted into the patient or after the needle has formed a portion of the tissue path between an external incision and a region of levator avulsion (in either direction), such as by accessing the needle tip through a vaginal incision. For instance, a needle may be inserted into and passed through an external incision (anterior or posterior), through a tissue path leading to a region of the levator avulsion, and the needle tip may be accessed through the vaginal incision to connect the needle tip to an end portion (e.g., connector) of an implant; when the needle is withdrawn a portion of the implant follows the needle and becomes placed in the tissue path. A portion of an implant can be placed in each of an anterior tissue path and a posterior tissue path by leading a needle through each tissue path, connecting the needle tip to an end portion (e.g., connector) of an implant, and withdrawing each needle.

An exemplary procedure for producing an anterior tissue path through an obturator foramen (left or right) between an anterior incision and a region of levator avulsion, can be performed using a single curved (e.g., helical) needle. The method can include a step of making a vaginal incision and dissecting from the vaginal incision to allow palpation of desired tissue such as the levator, levator avulsion, ischial spine, obturator internus muscle, and the medial edge of the inferior pubic ramus. One or both of the needle entry point and the levator avulsion can be separately palpated internally and externally with the thumb and index finger before marking a location for making the external incision. The edge of the inferior pubic ramus is palpated until it ends at the bottom of the obturator foramen. The skin incision can be marked at that location. An anterior incision can be made at a left side of the patient, at a right side of the patient, or both, depending on whether an implant is to be placed at either side or both sides. A needle, such as a helical needle, can be inserted through the anterior incision and led through the obturator foramen to a region of the levator avulsion, optionally so the tip of the needle extends into or toward the vaginal incision. The tip can be connected to an end of an implant and withdrawn to place a portion of the implant in the tissue path.

A posterior incision at a perirectal region can be generally posterior to and lateral to the rectum. Upon preparing the external incision, a tissue path can be prepared using an elongate needle (e.g., curved in two dimensions, meaning only two and not three dimensions). The tissue path can extend through the external incision optionally passing through dissected muscle, or perforating muscle of the posterior pelvic region, to a region of the levator avulsion or to the vaginal incision. As exemplary steps, a surgeon may access the posterior pelvic region (internally) through the vaginal incision, with rectovaginal dissection as necessary. A small (external) stab wound can be made in the perirectal region, e.g., about 3 centimeters lateral and 3 centimeters posterior to the anus. A needle (e.g., curved, e.g., in two dimensions) of an insertion tool can be inserted into the incision and pushed to puncture initial layers of tissue such as ischiorectal fossia. The needle can be passed further, e.g., through tissue of the gluteus muscle, past the rectum, and to a region of the vaginal incision or levator avulsion. The needle may either push a portion of implant through the tissue path from the external incision and into the posterior tissue path, or alternately may pull a portion of implant out through the tissue path (after a needle tip is connected to the implant such as in the region of the vaginal incision). Optionally when producing the tissue path or leading an implant through the tissue path, the surgeon can place a finger through the vaginal incision for palpation or to guide the tip of the needle.

An implant for use according to the present description can be any form of implant (e.g., "sling," "mesh," "tape," etc.) known or developed for use in pelvic treatments such as treatments of prolapse, urinary incontinence, fecal incontinence, conditions of the levator, etc.

An implant can generally include a support portion that contacts tissue to be supported, and two opposing end portions that extend away from the support portion. The terms "support portion" and "end portion" can be used specifically or generally to denote precise or general portions of an implant. When an implant has uniform size and shape from end to end, as does a simple mesh strip, the end portions will not necessarily exhibit a distinct boundary relative to the support portion.

Examples of implants useful for methods described herein include those described at United States Patent Applications 2006/0195007 (Ser. No. 11/346,750) the entirety of this document being incorporated herein by reference. Exemplary implants may be in the form of a continuous mesh tape that includes a support portion located at the center of the mesh, and two end portions, one end portion extending in each direction from the central support portion. Optionally and preferably the implant can include appurtenant features including one or more of a tensioning device (or "tensioning member") such as a suture or a sheath, and a connector or a dilating connector (e.g., "dilator") that removably or securely (e.g., permanently) engages a tip of a needle of an implantation tool. In various embodiments of devices and methods the implant may be a one piece mesh with the support portion substantially continuous with the two end portions, also optionally including a plastic sheath enclosing the implant, a tensioning suture running along all or a portion of the length of the implant, and one or two connectors or dilators (at the end of each end portion).

An example of an insertion tool that includes an elongate needle useful to prepare one or more of the tissue paths described herein is of the type described at United States Patent Applications 2005/0245787 (Ser. No. 10/834,943) and 2007/0068538 (Ser. No. 11/518,932), the entireties of these documents being incorporated herein by reference. Such tools generally include a handle and an elongate needle portion that is curved in two dimensions. The needle can be used to create a tissue path extending from one of the incisions, to a region of a levator avulsion, and through to the other incision (see e.g., FIGS. 3A through 3D). Alternately, this type of two-dimensionally curved needle may be useful to create a tissue path between a posterior (perirectal) incision and a region of a levator avulsion or a vaginal incision, and to place a portion of an implant in that tissue path.

Referring to FIGS. 4A and 4B, needle 14 and handle 10 are suitable for use as described herein. Handle 10 can be any suitable handle known in the art. U.S. Pat. No. 6,652,450, hereby incorporated by reference in its entirety, discloses several possible configurations. Needle 14 is generally curved or arcuate, preferably in two dimensions. A variety of needle designs or configurations may be used including, without limitation, straight, bent, curved, arc-shaped, Stamey, Raz and other configurations. The shape of needle 14 should facilitate and provide controlled passage of needle 14 through tissue as required. The end or tip of needle 14 is generally not sharpened but may be tapered to afford easy passage through tissue while providing a blunt surface that avoids cutting sensitive tissue such as the bowel. It is preferred that the diameter of needle 14 be small relative to the prior art to reduce tissue trauma. Needle tip 15 is optionally adapted to connect securely to a connector at an end of an end portion of an implant. Many different configurations of such a system are known and within the scope of the present invention. Several are disclosed in U.S. Pat. No. 6,652,450, which is incorporated by reference.

Examples of an insertion tool or "needle" useful to prepare one or more of the tissue paths described herein, especially an anterior tissue path that extends through an obturator foramen, are of the type described at United States Patent Applications 2003/0171644 (Ser. No. 10/306,179), 2005/0250977 (Ser. No. 10/840,646), and 2006/0195007 (Ser. No. 11/346,750), the entireties of these documents being incorporated herein by reference. These tools generally include a handle and an elongate needle. The needle extends from the handle along a straight portion (spacer) and then includes a three-dimensionally curved portion that may be in the form of a helical curve. See FIGS. 5A, 5B, 5C, and 5D.

A needle can be made of a malleable, yet durable, biocompatible surgical instrument materials such as, but not limited to, stainless steel, titanium, Nitinol, polymers, plastics and other materials, including combinations of materials. The needle should have sufficient structural integrity to withstand the various forces (e.g. forces caused by attachment to an implant, passage, and penetration or passage of the needle through the various tissues, without undergoing any significant structural deformation.

EXAMPLE

Reattachment and stabilization of levator ani avulsion injury in the treatment of genital prolapse:
1. The patient is placed in a lithotomy position, as for any vaginal pelvic surgery.
2. The vagina is opened along the posterior wall, from the vault to the rectovaginal septum.
3. The pararectal space is dissected.
4. The ischial spines on either side are palpated.
5. The avulsion level and sites are also palpated.
6. A transgluteal (posterior) needle pass is made similar to the Apogee needle (From American Medical Systems) pass, which includes inserting a two-dimensionally curved needle into an external incision in a perirectal region and perforating gluteal tissue.
7. Under digital guidance the needle is exited (from levator tissue) just at or above the avulsion area.
8. The graft (1.2 cm to 2 cm wide), preferably with a covering plastic, is attached to the exited needle and retrieved out of the posterior incision.
9. A transobturator needle is passed in the lowermost portion of the obturator foramen, similar to the inferior transobturator needle pass of the Perigee procedure (see U.S. patent application 2005/0250977). The needle needs to be palpated through the obturator internus muscle and does not need to go through the levator ani muscle.
10. The other end of the graft is then attached to this needle and exited out transcutaneous. The avulsion width is palpated.
11. Optionally a second graft parallel to the first graft can be inserted through the same transgluteal skin incision, but a bit more lateral and deeper towards the ischial spine.
12. The procedure can be repeated on the patient's opposite side. (The methods can be used for transvaginal, transobturator, or transgluteal levator stabilization using grafts, needles, or similar techniques to approximate (e.g., attach) the avulsed or detached levator muscle to its natural attachment point, and place a bar (implant) across to the levator muscle and attach the implant to the avulsed area as well.)
13. The implant tension is tested with the plastic sheath in place. The tensioning can be done unilaterally from only the obturator end, pulling the levator muscle toward the obturator internus muscle; this will prevent excessive shortening of the levator muscle.
14. Once all intended prolapse surgery is over tensioning can be done by pulling the obturator end of the graft, allowing the levator to abut and overlap the obturator internus. The friction/adhesiveness of the graft (implant) should hold the muscle in place while tissue ingrowth takes place.
15. The effectiveness of the surgery can be assessed intra-operatively and post-operatively using ultrasound.

Preliminary diagnosis of levator avulsion can be achieved using transperineal 4D ultrasound, MRI imaging, or a combination of these. the preliminary diagnosis, either type of imaging, and the procedure itself, can be unilateral or bilateral.

In a related embodiment, the sling/mesh can cover a large area of the levator ani muscle and lift the tissue up to the obturator. One or two strips of mesh can be used to attach to each obturator at or through the membrane. The mesh can be positioned along the pelvic side wall (lateral). An example of a useful mesh width can be about 1.5 cm to about 2 cm in width and can be in a kit with at least one helical needle, or with two helical needles and optionally one or two needles curved in two dimensions; the needles curved in two dimensions are non-helical and are curved in only two dimensions.

An exemplary kit can contain two needles for preparing two different anterior tissue paths starting at an anterior incision, passing through a right or a left obturator foramen and extending to a region of levator avulsion. The two anterior needles each exhibit a helical curve, each needle including a different helical curve, one for the right side anterior tissue path and one for the left side anterior tissue path. One needle can include a helical curve capable of creating a tissue path between a patient's left obturator foramen and a region of a levator avulsion on a patient's left side. The other needle can include a curve capable of creating a tissue path between a patient's right obturator foramen and a region of a levator avulsion on a patient's right side.

This type of or another kit can also or alternately include either one or two insertion tools for preparing one or two posterior tissue paths. These insertion tools can be curved in two dimensions and can be of the same shape. One needle can be included to prepare two tissue paths (a left side and a right side posterior tissue path), or two needles can be included, one for a left side posterior tissue path between a perirectal incision and a region of a levator avulsion and one for a right side posterior tissue path between a perirectal incision and a region of a levator avulsion.

In these or alternate kits, four implants (e.g., strips of mesh) can be included. Each implant can include a mesh strip, optional sheath along a length or along lengths of the implant or end portions thereof, one or more optional sutures extending along a length or along lengths of the implant or end portions thereof, and one connector at each end of each implant. Each connector can engage an end (tip) of an insertion needle.

The invention claimed is:
1. A method of treating a levator avulsion, the method comprising:
making a vaginal incision,
making a posterior incision,
making an anterior incision that allows access to an obturator foramen,
palpating levator muscle through the vaginal incision to identify a levator avulsion, making a posterior tissue path between the posterior incision and a region of levator muscle in a region of the levator avulsion, making an anterior tissue path between the anterior incision and the region of levator muscle, through the obturator foramen, providing an elongate implant comprising a support portion and two end portions, passing one of the two end portions through the anterior tissue path, passing one of the two end portions through the posterior tissue path, positioning the support portion to contact tissue of the levator muscle at a location in the region of the levator avulsion, and tensioning the implant to approximate tissue of the levator muscle, to support the levator muscle, and to relieve the levator avulsion.

2. The method of claim 1 wherein the posterior incision is lateral and posterior to the anus in skin of a buttock.

3. A method according to claim 1 wherein
the anterior incision is made at a location where an inferior edge of pubic ramus bone ends at a bottom of the obturator foramen, and
the anterior tissue path extends through the anterior incision, through an inferior third of the obturator foramen, through tissue of the obturator internus muscle, and to the region of levator muscle.

4. A method according to claim 1 comprising tunneling a portion of the implant through tissue of the levator muscle in a region of the levator avulsion.

5. A method according to claim 1 comprising tunneling a portion of the implant through tissue of the levator muscle in a region of the levator avulsion inferior to the levator avulsion.

6. A method according to claim 1 wherein
passing one of the two end portions of the implant through the posterior tissue path comprises:
inserting a needle into the posterior incision, through the posterior tissue path, to place an end of the needle at a position of access through the vaginal incision,
connecting a first of the two end portions with the end of the needle, and
withdrawing the needle from the posterior tissue path to pull the first of the two end portions through the vaginal incision and into the posterior tissue path; and
passing one of the two end portions of the implant through the anterior tissue path comprises:
inserting a needle into the anterior incision, through the anterior tissue path, to place an end of the needle at a position of access through the vaginal incision,
connecting a second of the two end portions with the end of the needle, and
withdrawing the needle from the anterior tissue path to pull the second of the two end portions through the vaginal incision and into the anterior tissue path.

7. A method according to claim 6 wherein the needle inserted into the anterior incision comprises a helical curve and the needle inserted into the posterior incision is curved in only two dimensions.

8. A method according to claim 1 wherein tensioning the implant comprises placing tension on the end portion extending through the anterior tissue path.

9. A method according to claim 1 wherein the method is performed on either a right side of a patient or a left side of a patient.

10. The method of claim 9 wherein the method is performed on a right side of the patient and on a left side of the patient.

11. A method according to claim 1 wherein the method is performed to place two implants on the same side of the patient, through the anterior incision and the posterior incision.

12. A method according to claim 1 comprising viewing the levator avulsion using an ultrasound method.

13. A method of treating a levator avulsion, the method comprising:
making a vaginal incision at a posterior of a vagina,
dissecting tissue of a pararectal space,
palpating levator tissue through the vaginal incision to identify a levator avulsion,
making a posterior incision lateral and posterior to the anus in a skin of a buttock,
making an anterior incision at a location where an inferior edge of pubic ramus bone ends at a bottom of an obturator foramen,
making a posterior tissue path between the posterior incision and a region of levator muscle in a region of the levator avulsion,
making an anterior tissue path between the anterior incision and the region of levator muscle, through the obturator foramen,
providing an elongate implant comprising a support portion and two end portions,
passing a portion of one end portion through the anterior tissue path,
passing a portion of the other end portion through the posterior tissue path,
positioning the support portion to contact tissue of levator muscle, and
tensioning the implant to approximate tissue of the levator muscle to support the levator muscle and relieve the levator avulsion.

* * * * *

UNITED STATES PATENT AND TRADEMARK OFFICE
CERTIFICATE OF CORRECTION

| | | |
|---|---|---|
| PATENT NO. | : 8,550,980 B2 | Page 1 of 1 |
| APPLICATION NO. | : 12/594408 | |
| DATED | : October 8, 2013 | |
| INVENTOR(S) | : Rane | |

It is certified that error appears in the above-identified patent and that said Letters Patent is hereby corrected as shown below:

In the Specification

In Column 3, Line 28, delete "DESCRIPTION" and insert -- DETAILED DESCRIPTION --, therefor.

In Column 5, Line 27, delete "ischorectal" and insert -- ischiorectal --, therefor.

In Column 12, Line 14, delete "these." and insert -- these --, therefor.

In the Claims

In Column 13, Line 21, in Claim 3, delete "A" and insert -- The --, therefor.

In Column 13, Line 29, in Claim 4, delete "A" and insert -- The --, therefor.

In Column 13, Line 32, in Claim 5, delete "A" and insert -- The --, therefor.

In Column 13, Line 35, in Claim 6, delete "A" and insert -- The --, therefor.

In Column 14, Line 4, in Claim 7, delete "A" and insert -- The --, therefor.

In Column 14, Line 8, in Claim 8, delete "A" and insert -- The --, therefor.

In Column 14, Line 11, in Claim 9, delete "A" and insert -- The --, therefor.

In Column 14, Line 18, in Claim 11, delete "A" and insert -- The --, therefor.

In Column 14, Line 22, in Claim 12, delete "A" and insert -- The --, therefor.

Signed and Sealed this
Twenty-fifth Day of August, 2015

Michelle K. Lee
*Director of the United States Patent and Trademark Office*

UNITED STATES PATENT AND TRADEMARK OFFICE
CERTIFICATE OF CORRECTION

PATENT NO. : 8,550,980 B2  
APPLICATION NO. : 12/594408  
DATED : October 8, 2013  
INVENTOR(S) : Ajay Rane Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1039 days.

Signed and Sealed this

Fifteenth Day of September, 2015

Michelle K. Lee
*Director of the United States Patent and Trademark Office*